United States Patent [19]

Niimura et al.

[11] Patent Number: 5,789,432
[45] Date of Patent: Aug. 4, 1998

[54] AROMATASE-INHIBITING COMPOSITION CONTAINING AZOLE DERIVATIVE

[75] Inventors: Koichi Niimura, Warabi; Akira Kato; Junko Miyagawa, both of Tokyo; Yuko Ikeda, Matsudo, all of Japan

[73] Assignee: Kureha Kagaku Kogyo Kabushiki Kaisha, Japan

[21] Appl. No.: 325,161

[22] Filed: Oct. 21, 1994

[30] Foreign Application Priority Data

Nov. 18, 1993 [JP] Japan ............ 5-311056

[51] Int. Cl.$^6$ ............ A61K 21/415; A61K 31/41
[52] U.S. Cl. ............ 514/399; 514/383; 514/396; 514/397
[58] Field of Search ............ 514/399, 383, 514/397, 396

[56] References Cited

U.S. PATENT DOCUMENTS

| | | | |
|---|---|---|---|
| 4,902,702 | 2/1990 | Enari et al. | 514/383 |
| 4,962,278 | 10/1990 | Enari et al. | 514/399 |
| 5,010,206 | 4/1991 | Enari et al. | 548/262.2 |
| 5,286,737 | 2/1994 | Kato et al. | 514/383 |

FOREIGN PATENT DOCUMENTS

| | | |
|---|---|---|
| 0 267 778 | 5/1988 | European Pat. Off. |
| 0 294 222 | 12/1988 | European Pat. Off. |
| 0 571 267 | 11/1994 | European Pat. Off. |
| 63-41476 | 2/1988 | Japan |
| 64-40480 | 2/1989 | Japan |

OTHER PUBLICATIONS

Database WPI, Week 9336, Derwent Publications Ltd., London, GB; AN 93–278159 & JP A 5 194 119 (Hokko Chemical Ind.) 3 Aug. 1993 Abstract.

Database WPI, Week 8813, Derwent Publications Ltd., London, GB; AN 88–089208 & JP A 63 041 479 (Kureha Chemical Ind.) 22 Feb. 1988 Abstract.

A Kato et al., Chem. Pahrm. Bull., 43, (12), pp. 2152–2158 (1995).

Angela M. H. Brodie et al., Breast Cancer Research and Treatment, 30, pp. 1–6 (1994).

Angela M. H. Brodie et al., Pharmac. Ther., 60, pp. 501–515 (1993).

T. Yamamoto et al., J. Steroid Biochem., 36, 6, pp. 517–521 (1990).

M. Jawed Iqbal et al., Clinical Science, 65, pp. 71–75 (1983).

M. DiMattina et al., Fertility and Sterility, 49, (1), pp. 62–65 (1988).

Paul A. J. Janssen et al., J. Med. Chem., 32, (10), pp. 2231–2239 (1989).

*Primary Examiner*—Jerome D. Goldberg
*Attorney, Agent, or Firm*—Parkhurst, Wendel & Burr, LLP

[57] ABSTRACT

The disclosure describes a pharmaceutical composition comprising an aromatase-inhibiting effective amount of a compound selected from the group consisting of compounds of the formula (I):

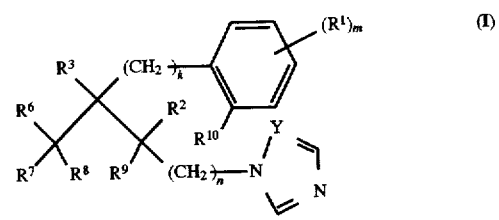

including their stereoisomers and salts thereof, wherein $R^1$ is halogen or phenyl; m is 0, 1, 2 or 3; k and n each are independently 0, 1 or 2; $R^2$ and $R^3$ each are independently H or OH; $R^6$ and $R^7$ each are independently H or $C_{1-4}$ alkyl; $R^8$ and $R^9$ each are H or $R^8$ and $R^9$ form —$C(R^4)(R^5)$—$C(R^{11})(R^{12})$— bond wherein $R^4$, $R^5$, $R^{11}$ and $R^{12}$ each are independently H or $C_{1-4}$ alkyl; Y is N or CH; and $R^{10}$ is H or halogen, or $R^{10}$ combines with $R^2$ to form —O— bond, with proviso that if $R^8$ and $R^9$ form —$C(R^4)(R^5)$—$C(R^{11})(R^2)$— bond, $R^3$, $R^6$ and $R^7$ each are H, and k and n each are 1, then $R^2$ and $R^{10}$ form —O— bond, and a pharmaceutically acceptable carrier or diluent.

2 Claims, No Drawings

AROMATASE-INHIBITING COMPOSITION CONTAINING AZOLE DERIVATIVE

BACKGROUND OF THE INVENTION

The present invention relates to an aromatase-inhibiting composition containing an azole derivative.

Estrogen, a sex hormone, is synthesized from androgenic steroids in the tissues such as ovary or placenta. In the biosynthetic pathway for the estrogen formation from an androgenic steroid, aromatization is essential, and aromatase takes part in such aromatization. It is therefore expected that if the aromatase can be effectively inhibited, estrogen-dependent diseases can be effectively treated (Cancer Research, Vol. 42, Suppl. 8, 3261s, 1982), and to this end certain aromatase inhibitors have been proposed.

4-Hydroxyandrostenedione is known as such an aromatase inhibitor. However, many of the steroid type drugs are generally attended with considerable side effects in practical use.

It is demanded to provide an aromatase inhibitor possessing an excellent inhibitory activity on the aromatase.

As a result of the present inventors' earnest studies, it has been found that azole derivatives having a non-steroidal chemical structure quite different from 4-hydroxyandrostenedione have an inhibitory activity on the aromatase. The present invention has been attained on the basis of this finding.

SUMMARY OF THE INVENTION

An object of the present invention is to provide an aromatase inhibiting composition containing an azole derivative which is low in toxicity (side effects) and shows a remarkable inhibitory activity on the aromatase.

To achieve the aim, in an aspect of the present invention, there is provided a pharmaceutical composition comprising an aromatase-inhibiting effective amount of a compound selected from the group consisting of compounds of the formula (I):

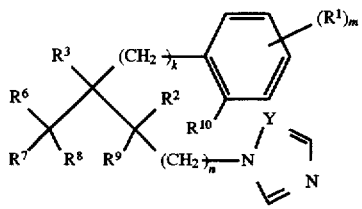

including their stereoisomers and salts thereof, wherein $R^1$ is halogen or phenyl; m is 0, 1, 2 or 3; k and n each are independently 0, 1 or 2; $R^2$ and $R^3$ each are independently H or OH; $R^6$ and $R^7$ each are independently H or $C_{1-4}$ alkyl; $R^8$ and $R^9$ each are H or $R^8$ and $R^9$ form —C($R^4$) ($R^5$)—C($R^{11}$) ($R^{12}$)— bond wherein $R^4$, $R^5$, $R^{11}$ and $R^{12}$ each are independently H or $C_{1-4}$ alkyl; Y is N or CH; and $R^{10}$ is H or halogen, or $R^{10}$ combines with $R^2$ to form —O— bond, with proviso that if $R^8$ and $R^9$ form —C($R^4$) ($R^5$)—C($R^{11}$) ($R^{12}$)— bond, $R^3$, $R^6$ and $R^7$ each are H, and k and n each are 1, then $R^2$ and $R^{10}$ form —O— bond, and a pharmaceutically acceptable carrier or diluent.

DETAILED DESCRIPTION OF THE INVENTION

The azole derivative according to the present invention is preferably an isolated single stereoisomer. The "stereoisomers" referred to herein include geometrical isomers, optical isomers and diastereoisomers.

The preferred combinations of the substituents in the above formula are as follows: $R^1$ is Cl, F or phenyl; m is 0, 1 or 2; k and n each are independently 0 or 1; $R^2$ and $R^3$ are as defined above; $R^6$ and $R^7$ each are independently H or $C_{1-2}$ alkyl; $R^8$ and $R^9$ form —C($R^4$) ($R^5$)—C($R^{11}$) ($R^{12}$)— bond, wherein $R^4$, $R^5$, $R^{11}$ and $R^{12}$ each are independently H or $C_{1-2}$ alkyl; and Y and $R^{10}$ are as defined above.

The more preferred combinations of the substituents are as specified below in (1) to (4).

(1) $R^1$ is Cl or Br; m is 0, 1 or 2; k and n each are independently 0 or 1; $R^2$, $R^8$, $R^9$ and $R^{10}$ each are H; $R^3$ is OH; $R^6$ and $R^7$ each are independently $C_{1-2}$ alkyl; and Y is N or CH.

(2) $R^1$ is Cl, Br or phenyl; m is 0, 1 or 2; k and n each are independently 0 or 1; $R^2$ and $R^{10}$ each are H; $R^3$ is OH; $R^6$ and $R^7$ each are independently H or $C_{1-2}$ alkyl; $R^8$ and $R^9$ form —$CH_2$—$CH_2$-bond; and Y is N or CH.

(3) $R^1$ is Cl or Br; m is 0, 1 or 2; k and n each are independently 0 or 1; $R^3$, $R^6$ and $R^7$ each are H; $R^8$ and $R^9$ form —$CH_2$—C($R^{11}$) ($R^{12}$)— bond, wherein $R^{11}$ and $R^{12}$ each are independently H or $C_{1-2}$ alkyl; $R^{10}$ and $R^2$ form —O— bond; and Y is N or CH.

(4) $R^1$ is Cl or Br; m is 0, 1 or 2; k is 1; n is 0 or 1; $R^3$, $R^6$ and $R^7$ each are H; $R^2$ is OH; $R^8$ and $R^9$ form —C($R^4$) ($R^5$)—$CH_2$— bond, wherein $R^4$ and $R^5$ each are independently $C_{1-2}$ alkyl; Y is N or CH; and $R^{10}$ is H or halogen, or $R^{10}$ combines with $R^2$ to form —O— bond.

The azole derivatives according to the present invention can be produced from the following processes.

Process A

In case no ring is formed by $R^8$ and $R^9$, and $R^2$ and $R^{10}$:

A preparation process of a compound of formula (I) is shown in Scheme 1.

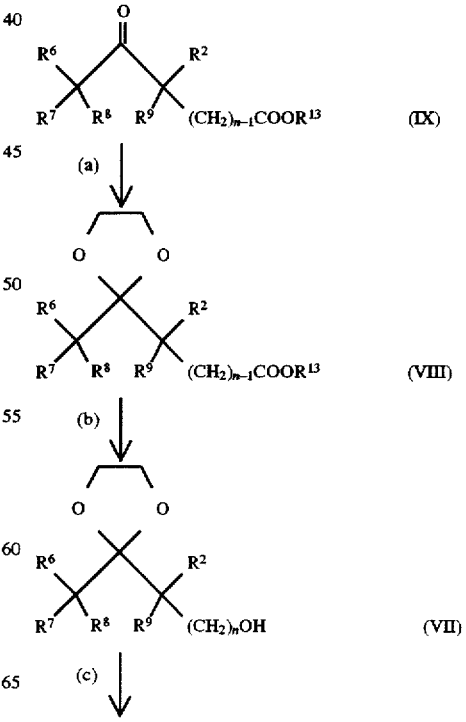

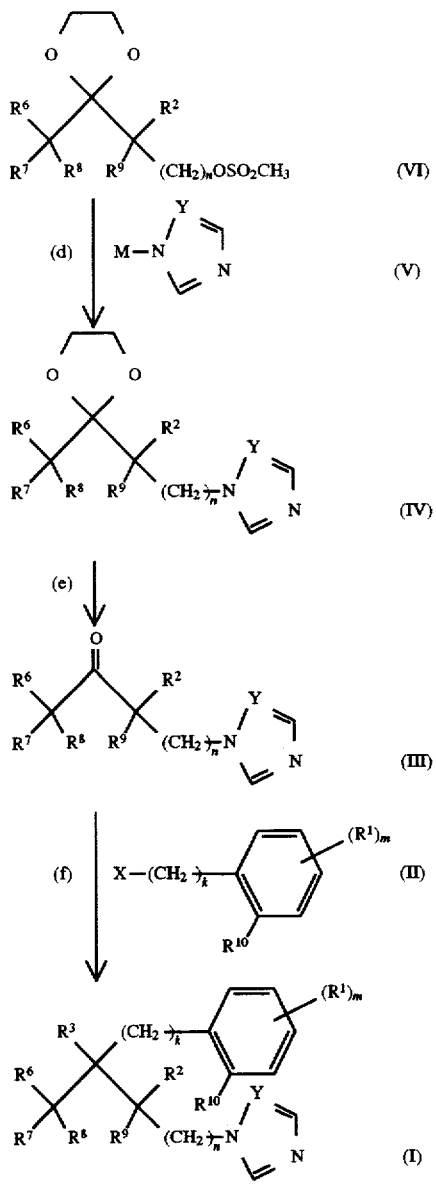

N or CH, at 40° to 100° C. to form a compound of formula (IV) wherein $R^2$, $R^6$, $R^7$, $R^8$, $R^9$, n and Y are as defined above.

Step (e)

The compound of formula (IV) is deketalated with an acid at 10° to 80° C. to form a compound of formula (III) wherein $R^2$, $R^6$, $R^7$, $R^8$, $R^9$, Y and n are as defined above.

Step (f)

The compound of formula (III) is reacted with a compound of formula (II) wherein X is halogen; $R^{10}$ is H or halogen; $R^1$ is halogen or phenyl; m is 0, 1, 2 or 3; and k is 0, 1 or 2, at −80° to +80° C. to obtain a compound of formula (I).

Process B-1

In case $R^8$ and $R^9$ form —C($R^4$) ($R^5$)—C($R^{11}$) ($R^{12}$)— bond and a phenyl derivative is used in the reaction:

The preparation steps are shown in Scheme 2.

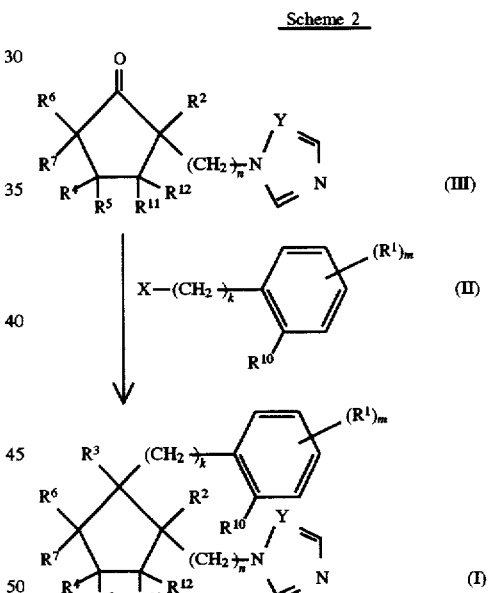

A compound of formula (II) wherein X is halogen, and k, m, $R^1$ and $R^{10}$ are as defined above, is added to an ether solution of magnesium. To the solution, a solution of a compound of formula (III) wherein $R^2$, $R^4$, $R^5$, $R^6$, $R^7$, $R^{11}$, $R^{12}$, n and Y are as defined above, is added dropwise and reacted at 5° to 20° C. to form a compound of formula (I). The compound of formula (III) can be derived from cyclopentanone.

Process B-2

In case $R^8$ and $R^9$ form —C($R^4$) ($R^5$)—C($R^{11}$) ($R^{12}$)— bond and an azole derivative is used in the reaction:

Step (a)

A compound of formula (IX) wherein $R^2$, $R^6$, $R^7$, $R^8$ and $R^9$ are as defined above; $R^{13}$ is $C_{1-3}$ alkyl; and n is 1 or 2, is reacted with ethylene glycol at 60° to 140° C. in the presence of p-toluenesulfonic acid to form a compound of formula (VIII) wherein $R^2$, $R^6$, $R^7$, $R^8$, $R^9$, n and $R^{13}$ are as defined above.

Step (b)

The compound of formula (VIII) is reacted with LiAlH$_4$ at −10° to +35° C. to form a compound of formula (VII) wherein $R^2$, $R^6$, $R^7$, $R^8$, $R^9$ and n are as defined above.

Step (c)

The compound of formula (VII) is reacted with methanesulfonyl chloride at −10° to +10° C. to form a compound of formula (VI) wherein $R^2$, $R^6$, $R^7$, $R^8$, $R^9$ and n are as defined above.

Step (d)

The compound of formula (VI) is reacted with a compound of formula (V) wherein M is H or a metal; and Y is The preparation steps are shown in Scheme 3.

Scheme 3

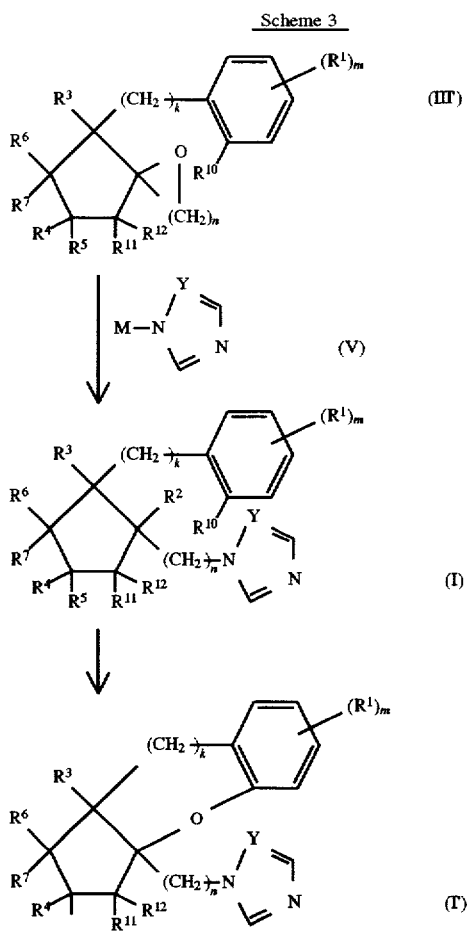

A compound of formula (III') wherein $R^1$, $R^3$, $R^4$, $R^5$, $R^6$, $R^7$, $R^{10}$, $R^{11}$, $R^{12}$, m and k are as defined above, is reacted with a compound of formula (V) wherein M and Y are as defined above, to form a compound of formula (I). The compound of formula (I) is reacted with a base, or the reaction is further advanced to obtain a compound of formula (I').

The compound of formula (III') can be obtained by reacting a ketone compound of the formula (IV'):

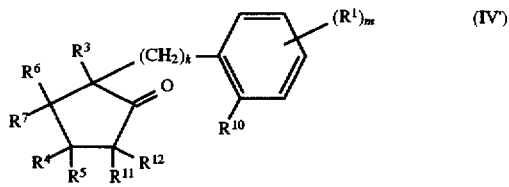

wherein $R^1$, $R^3$, $R^4$, $R^5$, $R^6$, $R^7$, $R^{10}$, $R^{11}$, $R^{12}$, m and k are as defined above, with, for example, dimethyloxosulfonium methylide or dimethylsulfonium methylide in case n=1, in the presence of a diluent.

The ketone compound of formula (IV') can be obtained from cyclopentanone-2-carboxylate and a corresponding substituted phenyl halide according to a known process (for example, Organic Syntheses, Vol. 45, 7, 1965).

The produced stereoisomers may be separated in each step. Separation of the stereoisomers can be accomplished by suitable means such as crystallization or chromatography, preferably optical active column chromatography.

Examples of the solvent used in the preparation of the compounds of formula (I) include ethers such as diethyl ether, diisopropyl ether and tetrahydrofuran; aromatic hydrocarbons such as benzene and toluene, containing ether; ethylene glycol; pyridine; and dimethylformamide. The reaction is preferably carried out with stirring. After termination of the reaction, the obtained reaction mixture is extracted with an organic solvent such as ethyl acetate, diethyl ether, chloroform, and benzene. The organic layer is separated, washed with water and dried, and then the solvent is distilled off under reduced pressure from the dried organic layer. The thus obtained residue may be immediately applied to further reaction, but it is preferably purified by suitable purification such as recrystallization or column chromatography before subjected to further reaction.

The present invention provide an aromatase-inhibiting composition characterized by containing a compound selected from the group consisting of azole derivatives represented by the formula (I), including their stereoisomers and salts thereof. The stereoisomer may be used either singly or as a mixture of two or more of them. They may also be used in the form of a pharmaceutically acceptable salt.

The aromatase-inhibiting activity was measured basically according to the method described in D. F. Covey et al: BBRC (I), 81–86, 1988. The aromatase-inhibiting activity of the azole derivatives used in the present invention was evaluated in terms of 50% aromatase activity-inhibiting concentration ($IC_{50}$) of the derivatives. The $IC_{50}$ was not more than $1\times10^{-8}$M for all of the derivatives.

The azole derivatives according to the present invention are useful as aromatase inhibitors and especially useful for the treatment of estrogen-dependent diseases such as breast cancer, benign breast disease, uterine cancer, pancreatic carcinoma and Cushing's syndrome.

The acute toxicity ($LD_{50}$) of the azole derivatives of formula (I) as determined by subcutaneous injection to mice is above 300 mg/kg.

The azole derivative according to the present invention can be administered through various routes such as oral, subcutaneous, intramuscular, intravenous, transdermal and rectal. It is usually used in the form of pharmaceutical compositions with a pharmaceutical acceptable carrier or diluent. For preparation of the compositions, the azole derivative (active ingredient) is usually mixed with a carrier, diluted with a carrier, or encapsulated in a carrier having a container form such as capsule. The carrier as a diluent, may be a solid, semi-solid or liquid material which serves as a vehicle, excipient or medium. Thus, the aromatase-inhibiting compositions of the present invention may be prepared into the form of tablet, pill, powder, elixir, emulsion, solution, syrup, suspension, aerosol, ointment, soft and hard gelatin capsules, suppository, sterile injectable solution and the like.

Examples of suitable carriers and diluents include lactose, dextrose, sucrose, sorbitol, mannitol, starch, calcium phosphate, calcium silicate, microcrystalline cellulose, polyvinylpyrrolidone, cellulose, polyoxyethylene sorbitan mono-oleate, gelatin, syrup, methyl cellulose, methyl hydroxybenzoate, propyl hydroxybenzoate, talc, magnesium stearate and water. The composition may additionally contain lubricant, wetting agent, emulsifying agent, suspending agent, antiseptic, sweetening agent, flavoring agent and the like.

For oral administration, for example, the azole derivative according to the present invention may be admixed with carriers or diluents and prepared into powders, or molded into tablets or encapsulated in gelatin capsules. The mixtures can alternatively be dissolved in liquids such as an aqueous glucose solution, isotonic sodium chloride solution, sterile water or the like.

The composition may be formulated in a unit dosage form which contains 0.01 to 500 mg, preferably 0.1 to 300 mg of the azole derivative. The composition is preferably formulated in a unit dosage form for administration.

The azole derivative according to the present invention is effective over a wide dosage range. For example, dosages per day will normally fall within the range of 0.005 to 100 mg/kg body weight. In the treatment of human adults, a range of about 0.1 to about 40 mg/kg, in single or divided doses, is preferred. However, it should be understood that the amount of the azole derivative actually administered will be determined by a skilled physician, in view of the relevant circumstances including the age of the patient, the severity of the patient and the route of administration. Therefore, the above dosage ranges are not intended to limit the scope of the invention in any way.

EXAMPLES

The following examples further illustrate the present invention.

Example 1

Preparation according to process A (1) Step (a): Preparation of ethyl 3,3-ethylenedioxy-4-methylpentanoate (VIII-1)

Ethyl 4-methyl-3-oxopentanoate (IX-1) (5.43 g), ethylene glycol (7.45 g) and p-toluenesulfonic acid (137.2 mg) were fed into an eggplant type flask (500 ml). Benzene was poured into the mixed solution, and the mixture was heated to reflux for 6 hours and the water was collected through a Dean-Stark trap. After completion of the reaction was confirmed by thin-layer chromatography (TLC), the eggplant type flask was transferred onto an ice bath. A few drops of triethylamine were added to the reaction solution to neutralize it. Distilled water (50 ml) was added to the reaction solution and the mixture was extracted once with 100 ml of ethyl acetate and twice with 150 ml of ethyl acetate.

The extract was washed with saturated brine, dried over anhydrous sodium sulfate and filtered, and the filtrate was concentrated under reduced pressure to obtain a crude product (6.84 g). The crude product was purified by silica gel chromatography (Kieselgel 60, 100 g, $\phi$=5.5 cm, n-hexane/ethyl acetate=6:1) to give the title compound (6.60 g).

Yield: 95.1%

$^1$H-NMR (CDCl$_3$, δ ppm): 0.96 (s, 3H), 0.97 (s, 3H), 1.27 (m, 3H), 2.12 (m, 1H), 2.67 (s, 2H), 3.96 (m, 2H), 4.02 (m, 2H), 4.14 (m, 2H).

IR (neat, cm$^{-1}$): 2990 s, 2900 m, 1740 s, 1370 w, 1185 m.

(2) Step (b): Preparation of 3,3-ethylenedioxy-4-methyl-1-pentan-1-ol (VII-1)

Lithium aluminum hydride (950 mg) and dry tetrahydrofuran (THF, 20 ml) were stirred at room temperature for 10 minutes in an eggplant type flask (100 ml). To the solution, the compound (VIII-1) (3.36 g) was added dropwise while cooled on an ice bath and the mixed solution was stirred overnight at room temperature in an argon stream. After completion of the reaction was confirmed by TLC, distilled water (30 ml) was added to the reaction solution on an ice bath to terminate the reaction. The reaction solution was filtered through Celite 535 and extracted with ethyl acetate. The extract was dried over anhydrous sodium sulfate, filtered and concentrated under reduced pressure. The resulting crude product (2.27 g) was purified by silica gel chromatography (Kieselgel 60, 30 g, $\phi$=3.0 cm, n-hexane/ethyl acetate=2:1) to give the title compound (2.09 g) as a transparent oily substance.

Yield: 78.6%.

$^1$H-NMR (CDCl$_3$, δ ppm) : 0.94 (s, 3H), 0.95 (s, H), 1.95 (m, 3H), 3.75 (t, 2H), 4.00 (m, 4H).

IR (neat, cm$^{-1}$): 3450 s, 2990 s, 2920 s, 1480 m, 1390 m, 1215 m.

(3) Step (c): Preparation of 3,3-ethylenedioxy-4-methylpentyl methanesulfonate (VI-1)

Methanesulfonyl chloride (320.2 mg) was placed in an eggplant type flask (100 ml) on an ice bath, followed by dropwise addition of the compound (VII-1) (405 mg) and further addition of pyridine (2 ml). The mixed solution was stirred in an argon stream. After completion of the reaction was confirmed by TLC, the reaction solution was allowed to stand for about three hours. HCl (1N) was added dropwise to the reaction solution to adjust its pH to around 6. The reaction solution was extracted with ethyl acetate (10 ml×2) and the extract was washed with saturated brine, dried over anhydrous sodium sulfate, filtered and concentrated under reduced pressure to give a crude product (590.2 mg).

Yield: 97.3%.

$^1$H-NMR (CDCl$_3$, δ ppm): 0.94 (s, 3H), 0.95 (s, 3H), 1.88 (m, 1H), 2.13 (t, 2H), 3.01 (s, 3H), 3.95 (s, 4H), 4.33 (t, 2H).

IR (neat, cm$^{-1}$): 3650 w, 3000 s, 2920 s, 1480 m, 1360 s, 1180 s.

(4) Step (d): Preparation of 3,3-ethylenedioxy-1-(1H-imidazol-1-yl)-4-methylpentane (IV-1)

Sodium salt of imidazole (V-1) (323 mg) and methylformamide (DMF, 3 ml) were placed in an eggplant type flask (200 ml), and then the compound (VI-1) (569.1 mg) were added, and the mixture was stirred at 50° C. for 3.5 hours on an oil bath. The oil bath was heated to 80° C. and the mixture was stirred. After completion of the reaction was confirmed by TLC, the reaction solution was extracted with diethyl ether (50 ml×2). The extract was washed with saturated brine, dried over anhydrous sodium sulfate, filtered and concentrated under reduced pressure. The resulting crude product (494.9 mg) was purified by silica gel chromatography (Kieselgel 60, 10 g, $\phi$=2.0 cm, n-hexane/ethyl acetate= 1:1) to give the title compound (IV-1) (448.9 mg) as white crystals.

Yield: 86.4%.

$^1$H-NMR (CDCl$_3$, δ ppm): 0.94 (s, 3H), 0.95 (s, 3H), 1.89 (m, 1H), 2.13 (t, 2H), 3.99 (m, 6H), 6.92 (s, 1H), 7.05 (s, 1H), 7.48 (s, 1H).

IR (KBr, cm$^{-1}$): 3120 s, 2990 s, 1520 s, 1460 s, 1385 s, 1235 s, 1189 s.

(5) Step (e): Preparation of 1-(1H-imidazol-1-yl)-4-methylpentan-3-one (III-1)

Sulfuric acid (1 ml), THF (2 ml) and distilled water (1 ml) were placed in an eggplant type flask (200 ml), and the compound (IV-1) (211 mg) was added. The mixture was stirred overnight at room temperature. After completion of the reaction was confirmed by TLC, the reaction solution was neutralized with saturated sodium hydrogen carbonate (28 ml) on an ice bath. The neutralized solution was extracted with ethyl acetate (50 ml×2), and the extract was washed with saturated brine, dried over anhydrous sodium sulfate, filtered and concentrated under reduced pressure to give the title compound (III-1) (159.9 mg) as a yellowish oily substance.

Yield: 95.8%.

$^1$H-NMR (CDCl$_3$, δ ppm): 1.05 (s, 3H), 1.06 (s, 3H), 2.53 (m, 1H), 2.90 (t, 2H), 4.25 (t, 2H), 6.89 (s, 1H), 7.02 (s, 1H), 7.47 (s, 1H).

IR (neat, cm$^{-1}$): 3420 s, 3000 s, 1715 s, 1520 m, 1475 m, 1390 m, 1235 m, 1080 m.

9

(6) Step (f): Preparation of (3R)-3-(4-chlorophenyl)-1-(1H-imidazol-1-yl)-4-methylpentan-3-ol (I-1)

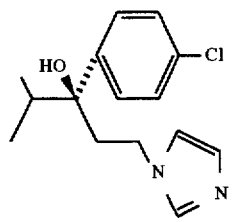

1-Bromo-4-chlorobenzene (II-1) (202 mg) and THF (1 ml) were placed in an eggplant type flask (200 ml), and n-butyl lithium (0.55 ml) was added dropwise at −78° C. in an argon stream. One hour later, a dry THF (1 ml) solution of the compound (III-1) (146.0 mg) was added dropwise. After completion of the reaction was confirmed by TLC, the reaction mixture was allowed to stand for 2 hours. The reaction was terminated with saturated ammonium chloride (20 ml) of −53° C. and the reaction mixture was heated to room temperature. Distilled water (3 ml) was added to the reaction solution and the solution was extracted with ethyl acetate (20 ml×3). The extract was washed with saturated brine, dried over anhydrous sodium sulfate, filtered and concentrated under reduced pressure. The thus obtained crude product (204.3 mg) was purified by silica gel chromatography (Kieselgel 60, 10 g, φ=2.0 cm, n-hexane/ethyl acetate/methanol=1:2:0.6) to give the title compound (I-1) (165.6 mg) as a white crystal.

Yield: 78.3%

$^1$H-NMR (CDCl$_3$, δ ppm): 0.69 (d, 3H), 0.98 (s, 3H), 2.04 (m, 1H), 2.24 (t, 1H), 2.33 (t, 1H), 3.50 (m, 1H), 3.95 (m, 1H), 6.79 (s, 1H), 7.00 (s, 1H), 7.32 (d, 2H), 7.33 (s, 1H), 7.36 (d, 2H).

IR (KBr, cm$^{-1}$): 3200 s, 2950 s, 1520 s, 1500 s, 1230 m, 1210 m, 1090 s.

(7) Step (f): Preparation of (3S)-3-(4-chlorobenzyl)-1-(1H-imidazol-1-yl)-4-methylpentan-3-ol (I-2)

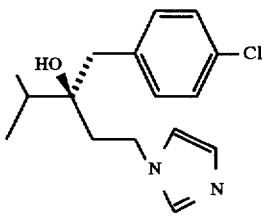

Magnesium (49 mg) and dry ether (2 ml) were placed in an eggplant type flask (200 ml), and 4-chlorobenzyl chloride (II-1) (306 mg) was added dropwise at room temperature in an argon stream. The mixed solution was stirred for 30 minutes and refluxed on an oil bath of 40° C. 15 minutes later, the solution was transferred onto an ice bath, and a dry THF/ether (1:1) solution (1 ml) of the compound (III-1) (170 mg) was added dropwise. 30 minutes later, the reaction solution was returned to room temperature and stirred overnight. After completion of the reaction was confirmed by TLC, the reaction was terminated with saturated ammonium chloride (5 ml). Cold water (5 ml) was added to the reaction solution and the solution was extracted with ethyl acetate (20 ml×2). The extract was washed with saturated brine, dried over anhydrous sodium sulfate and concentrated under reduced pressure. The resulting crude product (332.4 mg) was purified by silica gel chromatography (Kieselgel 60, 15 g, φ=3.5 cm, n-hexane/ethyl acetate/methanol=1:1:0.3) to give the title compound (I-2) (208.6 mg) as white crystals.

10

Yield: 71.2%.

$^1$H-NMR (CDCl$_3$, δ ppm): 0.98 (d, 3H), 1.04 (d, 3H), 1.78 (m, 2H), 2.00 (m, 1H), 2.66 (d, 1H), 2.86 (d, 1H), 3.98 (m, 1H), 4.05 (m, 1H), 6.85 (s, 1H), 7.03 (s, 1H), 7.15 (d, 2H), 7.30 (d, 2H), 7.44 (s, 1H).

IR (KBr, cm$^{-1}$): 3260 s, 2980 s, 2910 s, 1520 s, 1500 s, 1470 m, 1415 m, 1235 m, 1095 s.

Example 2

Preparation according to process B-1
Preparation of 1-(4-chlorobenzyl)-c-2-(1H-imidazol-1-ylmethyl)cyclopentan-r-1-ol (I-3) and its optical isomers (I-3 (+) and I-3 (−))

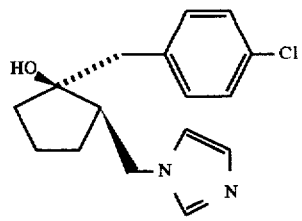

Magnesium (1.48 g) and dry ether (15 ml) were placed and stirred in an eggplant type flask (200 ml) at room temperature in an argon stream. To the solution was added dropwise a dry ether (40 ml) solution of 4-chlorobenzyl bromide (II-3) (12.5 g). The ether solution became cloudy, and it was confirmed that the Grignard reagent began to form. While refluxing ether gently at room temperature, the remaining ether solution of 4-chlorobenzyl bromide was added over a period of 25 minutes. The solution was stirred for 2 hours and transferred onto a water bath of 5 to 10° C. To the solution, a dry THF (50 ml) solution of 2-(1H-imidazol-1-ylmethyl)cyclopentan-1-on (III-3) (5.0 g) was added dropwise over a period of 10 minutes, followed by 2-hour stirring of the mixed solution. After disappearance of the starting materials was confirmed by TLC, the reaction solution was adjusted to pH 7 with aqueous HCl (1N) solution, cooled and, after addition of a small quantity of water, extracted with ethyl acetate. The organic layer was washed with saturated brine, dried over anhydrous sodium sulfate and concentrated under reduced pressure. The resulting crude product (8.83 g) was crystallized with n-hexane/ethyl acetate (1:1) to form the crude crystals (5.19 g), and these crude crystals (2 g) were purified by silica gel column chromatography (270 g, acetone/n-hexane=1:1) to give the title compound (I-3) (1.01 g) as white crystals.

Rf: 0.46 (ethyl acetate/n-hexane/methanol=5:3:1.5).

Mass spectrum: 290 (M$^+$).

$^1$H-NMR (CDCl$_3$, δ ppm) : 1.47 (m, 1H), 1.58 (m, 2H), 1.80 (m, 3H), 2.11 (m, 1H), 2.62 (s, 2H), 3.92 (dd, 1H), 4.16 (dd, 1H), 6.93 (s, 1H), 7.04 (s, 1H), 7.12 (d, 2H), 7.28 (d, 2H), 7.50 (s, 1H).

IR (KBr, cm$^{-1}$): 3158 s, 2990 s, 1600 w, 1585 w, 1525 s, 1508 s.

The produced compound (I-3) was subjected to optical active column chromatography (CHIRACEL OD, 20×250 mm, 10 μm, isopropanol/n-hexane=3:7, 10 ml/min) to separate peak 1 and peak 2, from which the white crystals (170 mg) corresponding to the respective peaks were obtained, respectively. These crystals were recrystallized from methanol/water to give the crystals of I-3 (−) (peak 1) (82.3 mg) and I-3 (+) (peak 2) (76.8 mg).

I-3 (−) (peak 1)

Melting point: 172°–173° C.

$[\alpha]_\lambda^{25}$: −31.3° (c=0.55, methanol)

I-3 (+) (peak 2)
  Melting point: 171°–172° C.
  $[\alpha]\lambda^{25}$: +32.2° (c=0.57, methanol).

Further, 1-(4-chlorobenzyl)-t-2-(1H-imidazol-1-ylmethyl)cyclopentan-r-1-ol (I-4) was separated by the column chromatography as white crystals.
  Rf: 0.41 (ethyl acetate/n-hexane/methanol=5:3:1.5).
  Mass spectrum: 290 (M$^+$).
  $^1$H-NMR (CDCl$_3$, δ ppm): 1.42 (m, 2H), 1.73 (m, 3H), 1.93 (m, 1H), 2.37 (m, 1H), 2.67 (d, 1H), 2.82 (d, 1H), 3.73 (dd, 1H), 4.30 (dd, 1H), 6.93 (s, 1H), 7.05 (s, 1H), 6.99 (d, 2H), 7.30 (d, 2H), 7.46 (d, 1H).
  IR (KBr, cm$^{-1}$): 3160 s, 3000 s, 1600 w, 1522 m, 1502 s.

The following compounds were prepared in the similar way:

1-(Benzyl)-t-2-(1H-imidazol-1-ylmethyl)cyclopentan-r-1-ol (I-5), m.p. 94°–98° C.
1-(4-Chlorobenzyl)-c-2-(1H-1,2,4-triazol-1-ylmethyl)cyclopentan-r-1-ol (I-6), m.p. 124°–126° C.
1-(2,4-Dichlorobenzyl)-c-2-(1H-1,2,4-triazol-1-ylmethyl)cyclopentan-r-1-ol (I-7), m.p. 104°–105° C.
1-(2,4-Difluorobenzyl)-c-2-(1H-1,2,4-triazol-1-ylmethyl)cyclopentan-r-1-ol (I-8), m.p. 99°–102° C.
1-(p-Biphenylmethyl)-c-2-(1H-1,2,4-triazol-1-ylmethyl)cyclopentan-r-1-ol (I-9), m.p. 150°–151° C.
1--(4-Chlorophenyl)-c-2-(1H-imidazol-1-ylmethyl)cyclopentan-r-1-ol (I-10), m.p. 128°–131° C.
1-(Phenyl)-c-2-(1H-imidazol-1-ylmethyl)cyclopentan-r-1-ol (I-11), m.p. 92°–95° C.
1-(4-Chlorophenyl)-c-2-(1H-1,2,4-triazol-1-ylmethyl)cyclopentan-r-1-ol (I-12), m.p. 103-105° C.

Example 3
Preparation according to process B-1
Preparation of nitrate of 1-(4-chlorobenzyl)-c-2-(1H-imidazol-1-ylmethyl)-cyclopentan-r-1-ol (I-13)

Compound (I-3) (0.1 g) was dissolved in THF and the solution was made acidic (pH 2) with 70% nitric acid. Diisopropyl ether was added dropwise to the solution to cause precipitation of white crystals. The crystals were filtered out to give the title compound (I-13).
  Mass spectrum: 354 (M$^+$+1), 290 (M$^+$—HNO$_3$).

Example 4
Preparation according to process B-2
Preparation of (3aR,9aR)-6-chloro-2,3,9,9a-tetrahydro-3,3-dimethyl-3a(1H)-(1H-1,2,4-triazol-1-ylmethyl)cyclopenta[b][1]benzopyran (I-14)

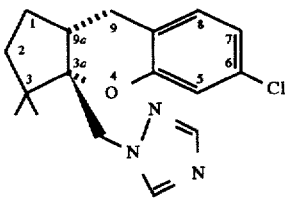

To anhydrous DMF (30 ml) in an eggplant type flask (200 ml), sodium hydride (670 ml, washed with anhydrous benzene) was added with stirring under a helium atmosphere. To the solution was added 1H-1,2,4-triazole (V) (1.8 g) and the mixed solution was stirred at room temperature till foaming ceased. To the resulting solution, an anhydrous DMF (10 ml) solution of 7-(2-fluoro-4-chlorobenzyl-4,4-dimethyl-1-oxaspiro[2,4]heptane (III-14) (5.00 g) was added dropwise and the mixture was stirred at 70° C. for 10 hours. The reaction solution was cooled, poured onto ice-cold water and extracted with ethyl acetate. The organic layer was washed with water and dried over anhydrous sodium sulfate and the solvent was distilled away under reduced pressure. The residue was purified by optical active column chromatography (CHIRACEL OD mfd. by Diacel Chem. Ind. Co., Ltd., isopropanol/n-hexane=3:7) to give the title compound (I-14) (1.5 g).
  $^1$H-NMR (CDCl$_3$, δ ppm): 0.80 (s, 3H), 1.12 (s, 3H), 1.12–3.07 (m, 7H), 4.17 (d, 1H), 4.43 (d, 1H), 6.73 (b, 3H), 8.70 (s, 1H), 8.83 (s, 1H).
  IR (KBr, cm$^{-1}$): 3060, 2940, 1595, 1570, 1480, 1130, 1020, 840, 740.
  $[\alpha]\lambda^{25}$: −24.8° (c=0.71, methanol).

The following compounds were synthesized in the similar way:

(3aR,9aR)-6-Chloro-2,3,9,9a-tetrahydro-3a(1H)-(1H-imidazol-1-ylmethyl)-3,3-dimethylcyclopenta[b][1]benzopyran (I-15), m.p. 108°–109° C.
(3aR,9aR)-6-Chloro-2,3,9,9a-tetrahydro-3a(1H)-(1H-imidazol-1-ylmethyl)cyclopenta[b][1]benzopyran (I-16), m.p. 87°–88° C.
(3aR,9aR)-6-Chloro-2,3,9,9a-tetrahydro-3a(1H)-(1H-1,2,4-triazol-1-ylmethyl)cyclopenta[b][1]benzopyran (I-17), m.p. 92°–94° C.
(3aR,9aR)-8-Fluoro-2,3,9,9a-tetrahydro-3a(1H)-(1H-1,2,4-triazol-1-ylmethyl)cyclopenta[b][1]benzopyran (I-18), m.p. 149°–151° C.

The following compounds were also obtained in the similar way:
c-2-(4-Chlorobenzyl)-1-(1H-imidazol-1-ylmethyl)-4,4-dimethylcyclopentan-r-1-ol (I-19), m.p. 139°–140° C.
c-2-(4-Chlorobenzyl)-4,4-dimethyl-1-(1H-1,2,4-triazol-1-ylmethyl)cyclopentan-r-1-ol (I-20), m.p. 84°–84.5° C.

Example 5
Acute toxicity

Acute toxicity was examined by subcutaneous administration to the ICR-JCL mice. Each of the compounds (I-1) to (I-20) was suspended in olive oil, and a determined amount of each suspension was syringed subcutaneously to the test mice. After administration, toxic symptoms of the mice were observed and LD$_{50}$ was determined from the number of deaths that occurred during the period of 7 days after administration. LD$_{50}$ was not less than 300 mg/kg for all of the compounds tested.

Example 6
Aromatase-inhibiting activity

The aromatase-inhibiting activity of each compound was measured according to the method of Covey et al: BBRC, 157 (1), 81–86, 1988. Radioactivity of a by-product H$^{14}$COOH released from a $^{14}$C-labeled substrate by the action of aromatase was measured to radiometrically determine aromatase-inhibiting activity of the compounds. The aromatase-inhibiting activity of the test compound is shown by 50% aromatase activity-inhibiting concentration (IC$_{50}$) of the compound.

An aromatase reaction system of the composition shown below in 67 mM phosphate buffer solution (0.5 ml) was incubated at 37° C. for 30 minutes with shaking. Chloroform (5 ml) was added to the reaction solution to stop the reaction. The reaction solution was vigorously stirred and then centrifuged to recover the by-product (H$^{14}$COOH) of the aromatase reaction in the aqueous layer. The aqueous layer (0.1 ml) was collected and mixed with a liquid scintillation cocktail (4 ml) to measure its radioactivity.

(1) Aromatase: Microsomes of human placenta (0.1 mg/ml, protein concentration).

(2) Substrate: [19-$^{14}$C] 4-Androstene-3,17-dione (1×10$^{-6}$M; 2 kBq/ml).

(3) Coenzymes: Nicotinamide adenine dinucleotide phosphate, reduced form (2×10$^{-3}$M), glucose-6-phosphate (4×10$^{-3}$M) and glucose-6-phosphate dehydrogenase (4 U/ml).

(4) Test compound

Radioactivity of the reaction system exclusive of (1) was supposed to be background radioactivity as 100% control of aromatase inhibition. Radioactivity of the reaction system exclusive of (4) was supposed to be that of negative control as 0% of aromatase inhibition. Based on the results of the measurements, a graph of the concentration of the test compounds vs. the aromatase inhibiting activity was produced, and the IC$_{50}$ was determined from the graph. 4-Hyroxyandrostenedione was used as a reference compound.

The results are shown in Table 1. The Compound Nos. correspond to those given in the Examples 1–5.

TABLE 1

| Comp. No. | IC$_{50}$ (M) |
|---|---|
| I-1 | 1.0 × 10$^{-8}$ |
| I-2 | 1.0 × 10$^{-8}$ |
| I-3 | 4.0 × 10$^{-8}$ |
| I-4 | 2.0 × 10$^{-8}$ |
| I-5 | 5.0 × 10$^{-8}$ |
| I-6 | 4.0 × 10$^{-8}$ |
| I-7 | 1.0 × 10$^{-8}$ |
| I-8 | 1.2 × 10$^{-8}$ |
| I-9 | 1.3 × 10$^{-8}$ |
| I-10 | 3.0 × 10$^{-8}$ |
| I-11 | 3.5 × 10$^{-8}$ |
| I-12 | 1.0 × 10$^{-8}$ |
| I-13 | 5.5 × 10$^{-8}$ |
| I-14 | 1.2 × 10$^{-8}$ |
| I-15 | 4.5 × 10$^{-8}$ |
| I-16 | 3.0 × 10$^{-8}$ |
| I-17 | 3.0 × 10$^{-8}$ |
| I-18 | 1.3 × 10$^{-8}$ |
| I-19 | 6.5 × 10$^{-8}$ |
| I-20 | 4.0 × 10$^{-8}$ |
| Reference | 2.0 × 10$^{-8}$ |

Example 7

Aromatase inhibiting activity of optical isomers

The aromatase inhibiting activities (IC$_{50}$) of the optical isomers (I-3 (−) and I-3 (+)) were determined in the same way as in Example 6. IC$_{50}$ of I-3 (−) was 4.0×10$^{-9}$M and that of I-3 (+) was 8.0×10$^{-8}$M.

Example 8

| Formulation example | |
|---|---|
| Compound (I-1) | 100 mg |
| Polyoxyethylene sorbitan mono-oleate | 50 mg |
| Starch | 250 mg |

The composition was mixed well and encapsulated in a capsule.

What is claimed is:

1. A method of treating any one of breast cancer, benign breast disease, uterine cancer, pancreatic carcinoma and Cushing's syndrome, which comprises administering to a patient suffering therefrom, an aromatase-inhibiting effective amount of a compound selected from the group consisting of compounds of the formula (I):

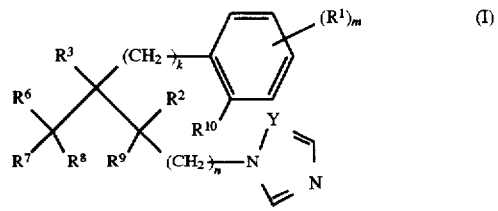

including their stereoisomers and salts thereof, wherein $R^1$ is halogen or phenyl; m is 0, 1, 2 or 3; k and n each are independently 0, 1 or 2; $R^2$ and $R^3$ each are independently H or OH; $R^6$ and $R^7$ each are independently H or $C_{1-4}$ alkyl; $R^8$ and $R^9$ each are H or $R^8$ and $R^9$ form —C($R^4$) ($R^5$)—C($R^{11}$) ($R^{12}$)— bond wherein $R^4$, $R^5$, $R^{11}$ and $R^{12}$ each are independently H or $C_{1-2}$ alkyl; Y is N or CH; and $R^{10}$ is H or halogen, or $R^{10}$ combines with $R^2$ to form —O— bond, with proviso that if $R^8$ and $R^9$ form —C($R^4$) ($R^5$)—C($R^{11}$) ($R^{12}$)— bond, $R^3$, $R^6$ and $R^7$ each are H, and k and n each is 1, then $R^2$ and $R^{10}$ form —O— bond.

2. A method according to claim 1, wherein the compound is 1-(4-chlorobenzyl)-c-2-(1H-imidazol-1-ylmethyl) cyclopentan-r-1-ol.

* * * * *